(12) United States Patent
Ishida et al.

(10) Patent No.: US 6,372,278 B1
(45) Date of Patent: Apr. 16, 2002

(54) SWEETENER COMPOSITION

(75) Inventors: Hirotoshi Ishida; Akihiro Kishishita; Takeshi Nagai; Kazutaka Nagashima; Atsuhiko Hirano, all of Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/707,953

(22) Filed: Nov. 8, 2000

Related U.S. Application Data

(63) Continuation of application No. PCT/JP99/02198, filed on Apr. 26, 1999.

(30) Foreign Application Priority Data

May 8, 1998 (JP) ............................................ 10-125989

(51) Int. Cl.$^7$ .............................................. A23L 1/236
(52) U.S. Cl. ........................ 426/548; 426/590; 560/40
(58) Field of Search ................................ 426/548, 590; 560/39, 40, 41

(56) References Cited

U.S. PATENT DOCUMENTS

| | | | |
|---|---|---|---|
| 5,480,668 A | * | 1/1996 | Nofre et al. ................. 426/548 |
| 6,048,999 A | * | 4/2000 | Pajor et al. ................... 560/39 |

FOREIGN PATENT DOCUMENTS

| | | |
|---|---|---|
| JP | 8-503206 | 4/1996 |
| JP | 10-248520 | 9/1998 |

* cited by examiner

*Primary Examiner*—Leslie Wong
(74) *Attorney, Agent, or Firm*—Oblon, Spivak, McClelland, Maier & Neustadt, P.C.

(57) ABSTRACT

One embodiment of the present invention provides a sweetener composition, which includes N-{N-(3,3-dimethylbutyl)-L-α-aspartyl}-L-phenylalanine 1-methyl ester, and Aspartame, wherein a ratio of the Aspartame to a total amount of the Aspartame and the N-{N-(3,3-dimethylbutyl)-L-α-aspartyl}-L-phenylalanine 1-methyl ester is in the range of 10 to 99.5% by weight, methods of making and of using. Another embodiment of the present invention provides a method for preparing a sweetener composition, which includes drying an A-type crystal of N-{N-(3,3-dimethylbutyl)-L-α-aspartyl }-L-phenylalanine 1-methyl ester to obtain a C-type crystal of N-{N-(3,3-dimethylbutyl)-L-α-aspartyl }-L-phenylalanine 1-methyl ester. Another embodiment of the present invention provides a method for producing a sweetener, which includes admixing N-{N-(3,3-dimethylbutyl)-L-α-aspartyl }-L-phenylalanine 1-methyl ester with Aspartame, wherein a ratio of the Aspartame to a total amount of the N-{N-(3,3-dimethylbutyl)-L-α-aspartyl }-L-phenylalanine 1-methyl ester and the Aspartame is in the range of 10 to 99.5% by weight. Another embodiment of the present invention provides a method for improving the dissolution rate of N-{N-(3,3-dimethylbutyl)-L-α-aspartyl }-L-phenylalanine 1-methyl ester, which includes, prior to dissolving the N-{N-(3,3-dimethylbutyl)-L-α-aspartyl }-L-phenylalanine 1-methyl ester, admixing the N-{N-(3,3-dimethylbutyl)-L-α-aspartyl }-L-phenylalanine 1-methyl ester with Aspartame, wherein a ratio of the Aspartame to a total amount of the N-{N-(3,3-dimethylbutyl)-Lα-aspartyl}-L-phenylalanine 1-methyl ester and the Aspartame is in the range of 10 to 99.5% by weight.

16 Claims, 2 Drawing Sheets

US 6,372,278 B1

SWEETENER COMPOSITION

This application is a continuation of PCT/JP99/02198, which was filed Apr. 26, 1999.

BACKGROUND OF THE INVENTION

1. Field of the Invention

The present invention relates to a sweetener composition having excellent solubility, which includes N-{N-(3,3-dimethylbutyl)-L-α-(aspartyl}-L-phenylalanine 1-methyl ester (Neotame, abbreviated hereinafter to "NM") and Aspartame (abbreviated hereinafter to "APM") as active ingredients.

2. Discussion of the Background

It is reported that the sweetness strength or sweetening potency of the synthetic high-potency sweetener, NM, is about 10,000 times that of sucrose in terms of weight ratio (Japanese Patent Kohyou Publication JP-A-8-503206). The properties of sweetness quality for NM are not reported in detail, but the present inventors have found that such a compound has an extremely weak early taste (i.e., wherein the sweetener, when put in the mouth, tastes sweet as early as sucrose), and is extremely strong in later taste (i.e., wherein the sweetener tastes sweet later than sucrose). Further, NM has a strong astringent taste. Accordingly, the balance of the quality of sweetness properties for NM is poor when compared to sucrose. Sucrose is generally regarded as the standard for evaluating the properties or characteristics of the quality of sweetness.

It is also reported that the sweetness strength of the amino acid type synthetic sweetener, APM, is about 200 times that of sucrose in weight ratio (See Japanese Patent Kokoku Publication JP-B-47-3 1031). APM has a sweetness quality characterized by a weak early taste and a strong later taste as compared with sucrose.

Various proposals have been made for the improvement in quality of the sweetness of NM and APM, particularly for the improvement in quality of the sweetness of the latter, thus achieving considerable effects. However, NM and APM have a further problem with dissolution characteristics; that is, NM and APM powders (crystalline raw powders) have poor dissolution characteristics in water (that is, they are not readily dissolved due to their easy formation of agglomerates, or their dissolution rate is low, etc.). Poor dissolution characteristics, which may result from the formation of agglomerates, or the like is significantly disadvantageous to industrial production, since the production yield of foods and drinks such as soft drinks that contain NM or APM to confer sweetness is undesirably reduced.

For improvement of the dissolution rate of APM, various proposals using pelletizing methods (granulations) have been made. However, these methods are not satisfactory in that they require further improvement of dissolution rate (See Japanese Patent Kokai Publication JP-A-4-346769 etc.) and require the simultaneous use of a relatively large amounts of excipients (See Japanese Patent Kokai Publications JP-A-49-126855, JP-A-50-19965, JP-A-57150361 etc.).

SUMMARY OF THE INVENTION

Accordingly, one object of the present invention is thus to improve the dissolution rate of NM and APM.

The present inventors have unexpectedly found that the dissolution rate of NM, and particularly that of a specific crystal of NM (which may be also called "C-type crystal") is improved by APM in a certain range, and vice versa, and further that the dissolution rate of a mixture of both of them at a specific mixing range is higher than not only that of NM alone but also that of APM alone, and this phenomenon is particularly remarkable and significant when NM is in the form of C-type crystal.

Accordingly, one embodiment of the present invention provides a sweetener composition, which includes:

N-{N-(3,3-dimethylbutyl)-L-α-aspartyl}-L-phenylalanine 1-methyl ester; and

Aspartame, wherein a ratio of the Aspartame to a total amount of the Aspartame and the N-{N-(3,3-dimethylbutyl)-L-α-aspartyl}-L-phenylalanine 1-methyl ester is in the range of 10 to 99.5% by weight.

Another embodiment of the present invention provides a drink composition, which includes:

a mixture of N-{N-(3,3-dimethylbutyl)-L-α-aspartyl}-L-phenylalanine 1-methyl ester;

Aspartame; and a potable liquid, wherein a ratio of the Aspartame to a total amount of the N-{N-(3,3-dimethylbutyl)-L-α-aspartyl}-L-phenylalanine 1-methyl ester and the Aspartame is in the range of 10 to 99.5% by weight.

Another embodiment of the present invention provides a method for preparing a sweetener composition, which includes:

drying an A-type crystal of N-{N-(3,3-dimethylbutyl)-L-α-aspartyl}-L-phenylalanine 1-methyl ester to obtain a C-type crystal of N-{N-(3,3-dimethylbutyl)-L-α-aspartyl}-L-phenylalanine 1-methyl ester.

Another embodiment of the present invention provides a method for producing a sweetener, which includes:

admixing N-{N-(3,3-dimethylbutyl)-L-α-aspartyl}-L-phenylalanine 1-methyl ester with Aspartame, wherein a ratio of the Aspartame to a total amount of the N-{N-(3,3-dimethylbutyl)-L-α-aspartyl}-L-phenylalanine 1-methyl ester and the Aspartame is in the range of 10 to 99.5% by weight.

Another embodiment of the present invention provides a method for improving the dissolution rate of N-{N-(3,3-dimethylbutyl)-L-α-aspartyl}-L-phenylalanine 1-methyl ester, which includes, prior to dissolving the N-{N-(3,3-dimethylbutyl)-L-α-aspartyl }-L-phenylalanine 1-methyl ester, admixing the N-{N-(3,3-dimethylbutyl)-L-α-aspartyl}-L-phenylalanine 1-methyl ester with Aspartame, wherein a ratio of the Aspartame to a total amount of the N-{N-(3,3-dimethylbutyl)-L-α-aspartyl}-L-phenylalanine 1-methyl ester and the Aspartame is in the range of 10 to 99.5% by weight.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
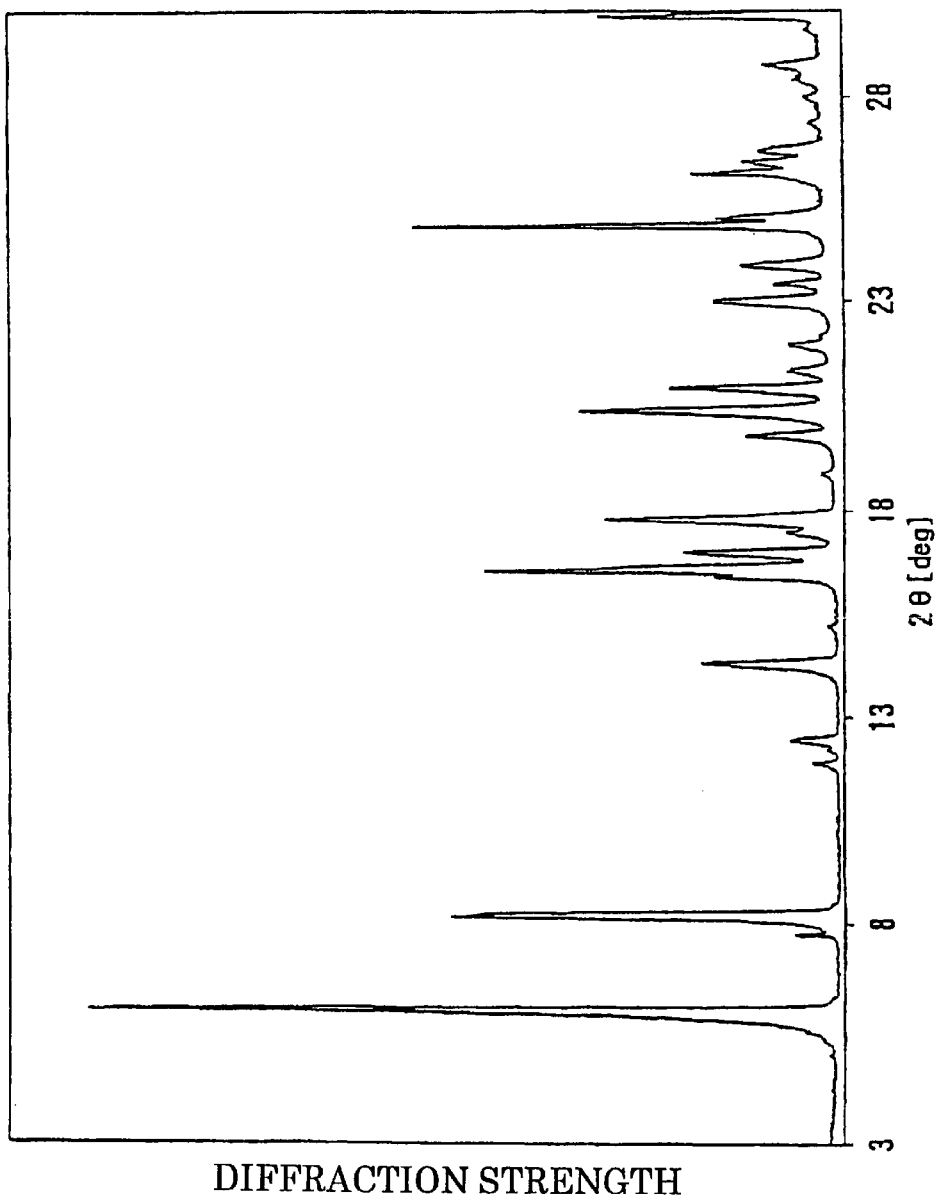
FIG. 1: A powder X-ray diffraction pattern of A-type crystals.

Various other objects, features and attendant advantages of the present invention will be more fully appreciated as the same becomes better understood from the following detailed description of the preferred embodiments of the invention.

Preferably, the NM is in the form of a powder or crystals in the mixture. Likewise, the APM is preferably in the form of a powder or crystals in the mixture. Preferably, the mixture itself is in the form of a powder or crystals. Most preferably, the powder and/or crystals is a dry, free-flowing powder or crystals.

The crystalline form of powdery NM that is one of the active ingredients in the novel sweetener composition of the present invention is not particularly limited. For example, it may be either the known crystals (which may be also called "A-type crystal(s)") or the "C-type" crystal(s) described below. The C-type is significantly superior to the former and is thus most preferred.

In an additional remark, the crystal structure of known NM as disclosed in W095/30689, the entire contents of which are hereby incorporated by reference, is described as IR spectrum data therein. Further, the present inventors analyzed the structure of its single crystal, and as a result, they confirmed that this crystal is a monohydrate, and when measured by powder X-ray diffractometry, the crystal shows characteristic peaks in diffractive X-ray (X-ray diffraction pattern) at diffraction angles of at least 6.0°, 24.8°, 8.2°, and 16.5° (2θ, CuKα radiation (ray;line)). For the sake of convenience, the present inventors referred to this crystal as "A-type crystal".

The present inventors have also found that the water content of dry A-type crystal is usually in the range of 3 to 6% by weight (including crystal water), but if this A-type crystal is further dried until its water content is reduced to less than 3%, a novel crystal of N-(3,3-dimethylbutyl)-APM with improved dissolution rate wherein the crystal water has been eliminated, is obtained, and this novel crystal was referred to as "C-type crystal".

Thus, a preferred embodiment of the present invention provides a novel form of N-{N-(3,3-dimethylbutyl)-L-α-aspartyl}-L-phenylalanine 1-methyl ester, which is referred to herein as the "C-type crystal", methods of making, and methods of use.

When measured by powder X-ray diffractometry (using CuKαradiation), this C-type crystal shows characteristic peaks in the X-ray diffraction pattern at diffraction angles different from those of the A-type crystal, that is, at diffraction angles (2θ) of at least 7.1°, 19.8°, 17.3°, and 17.7°. Reference is made to Reference Examples 1 to 3 below.

APM that is the other active ingredient in the novel powdery sweetener composition of the present invention can be used in the form of e.g. the hydrated crystals, to which it is not particularly limited. Preferably, the APM is in the form of a dry, free-flowing powder.

The mixing ratio of NM and APM used in the novel sweetener composition of the present invention is in the range of 10 to 99.5% by weight in terms of the ratio of APM to 5 the total amount of both NM and APM. If the ratio of APM used therein is less than 10% by weight, the effect of APM on the promotion of NM dissolution is decreased, whereas with the ratio of more than 99.5% by weight, the effect of APM on the promotion of NM dissolution is hardly observed. More preferably, the mixing ratio ranges from 20 to 97%, more particularly preferably, the mixing ratio is 50 to 97%, more particularly preferably 55 to 10 95%, most preferably 60 to 90%, and most particularly preferably 75 to 85%. These ranges include all values and subranges therebetween, including 12%, 18%, 22%, 35%, 45%, 58% and 91%.

C-type crystals, when mixed with APM in the range of 10 to 99.5%, have significant promoting effect on dissolution rate and are thus superior to A type crystals, as can be seen from Tables 1 and 2 below. If C-type crystals are used as powdery NM, the ratio of APM to the total amount of NM and APM used therein is preferably in the range of 10 to 97% by weight, and more preferably 20 to 97%, more particularly preferably, the mixing ratio is 50 to 97%, more particularly preferably 55 to 95%, most preferably 60 to 90%, and most particularly preferably 75 to 85%. These ranges include all values and subranges therebetween, including 12%, 18%, 22%, 35%, 45%, 58% and 91%.

The dissolution rate of a mixture of NM C-type crystals and APM in the range of 10 to 90% by weight of APM thereto is higher than that of NM A-type crystals alone, and the dissolution rate of a mixture of NM C-type crystals and APM in the range of 50 to 97% by weight of APM thereto is higher than the dissolution rate of not only that of NM C-type crystals alone but also that of APM alone. Each of the above ranges includes all values and subranges therebetween, including 12%, 18%, 22%, 35%, 45%, 58% and 89%.

If NM and APM are separately and at the same time added to water (i.e., separate but simultaneous addition) without being previously mixed, preferably at the predetermined ratio, neither NM nor APM affect their mutual dissolution rate, and in this case, the dissolution rate as a whole is low but identical to the dissolution rate of one of them which has a lower dissolution rate when used alone. See, e.g., Experimental Example 3 below.

For the purpose of easy application or improvement in quality of sweetness, the novel sweetener composition of the present invention, similar to the case of conventional high-potency sweetener compositions, can incorporate diluents (thinners) and excipients such as sugar alcohols, oligosaccharide, food fibers (dietary fibers) and the like, or other synthetic high-potency sweeteners such as Alitame, saccharin, Acesulfame K etc. as necessary in an amount within such a range as not to spoil the NM and APM dissolution rate (solubilities) improved by the present invention. The diluents and excipients in this case include low-potency sweeteners such as sucrose, glucose or the like.

The sweetener composition according to the present invention is particularly suitable for use in food and drink compositions for human and animal consumption. Preferred examples include without limitations beverages, table-top sweeteners, sweetener packets, candies, ice cream, coffee, tea, cereal, liquid sweeteners, low-calorie sweeteners, gelatin desserts, bread, cookies, fruit flavored beverages, cake mixes, fruit juices, syrups, salad dressings, pet foods, carbonated and non-carbonated soft drinks, foodstuffs, and the like. The composition of the present invention is also suitable for other applications such as cough medicines, cough drops and tonics. The composition of the present invention may be suitably mixed with a diluent or solvent including aqueous-based, alcohol-based, mixed aqueous/alcohol-based, water, propylene glycol, a water/propylene glycol mixture, ethanol or a water/ethanol mixture. Preferably, the sweetener composition of the present invention may be used alone or will make up anywhere from 0.1% to greater than 99% by weight of the food or drink composition, more preferably 1–95%, more particularly preferably 2–90%, more especially preferably 5–85%, most preferably 10–75%, most particularly preferably 20–65%, and most especially preferably 30–55% by weight, based on the total weight of the food or drink composition. These ranges include all values and subranges therebetween, including 4%, 14%, 22%, 43%, 49%, 82% and 91%.

EXAMPLES

Having generally described this invention, a further understanding can be obtained by reference to certain specific examples which are provided herein for purposes of illustration only and are not intended to be limiting unless otherwise specified. The amounts are given as percentages by weight, except where otherwise mentioned.

Reference Example 1
Preparation of NM

The following were introduced successively under stirring to a reactor equipped with an agitating blade for ensuring very efficient transfer of gaseous hydrogen to a liquid layer. That is, 700 ml ion exchanged water, 4.21 ml of acetic acid, 20 g of 10% palladium carbon, 1,300 ml of methanol, 56 g of Aspartame and 25 ml of 3,3-dimethylbutylaldehyde were introduced.

The reactor was filled with a nitrogen gas stream, and then the reaction mixture was hydrogenated at a $H_2$ gas flow rate of 200 ml/min. at room temperature. The progress of this reaction was monitored by sampling the reaction mixture and analyzing the product in high performance liquid chromatography (HPLC). After the hydrogenation reaction for 6 hours, this reaction was terminated by filling the reactor with a nitrogen gas and filtering the reaction mixture through a fine pore filter (0.45 $\mu$m) to remove the catalyst.

As a result of the analysis of the resulting filtrate (1,494 g), the yield was 81%. Subsequently, this filtrate was concentrated to 281 g to remove the methanol, and crystals were precipitated under stirring at 10° C. overnight. Finally, 87 g white wet crystals of NM (yield: 77%) were obtained at a high purity (99% or more, HPLC)

Reference Example 2
Production of A-type crystals

A part of NM prepared in Reference Example 1 was used to prepare 100 g aqueous solution of NM at a concentration of 3% by weight (dissolved at 60° C.) . Then, the solution was cooled from 60° C. to 30° C. for 5 minutes under stirring. When the liquid temperature was reached to 30° C., crystallization of white crystals was initiated. After overnight aging under the liquid temperature kept at 30° C., the crystals were collected on a filter paper.

(a) The diffractive X-ray (X-ray diffraction pattern) of the wet crystals obtained above was measured by powder X-ray diffractometry (diffractometer) using CuK$\alpha$ ray(radiation). The obtained powder X-ray diffraction pattern is shown in FIG. 1.

As is evident from the pattern of the figure, the wet crystals showed characteristic diffraction peaks at least 6.0°, 24.8°, 8.2°and 16.5°, and they were A-type crystals.

Further, (b) the wet crystals were placed in a vacuum dryer set at 50° C., and dried until their water content was reduced to 5% by weight. The dried crystals thus obtained were measured by powder X-ray diffractometer using CuK$\alpha$ Radiation (ray) , indicating that the crystals were A-type crystals as well.

Further, as a result of IR spectrum (KBr) measurement, its values agreed with those described in WO95/30689, the entire contents of which being hereby incorporated by reference.

Reference Example 3
Production of C-type crystals

The dried A-type crystals with a water content of 5% by weight described above were continued to be dried in the vacuum dryer until their water content was reduced to 0.8% by weight.

Figure 2:
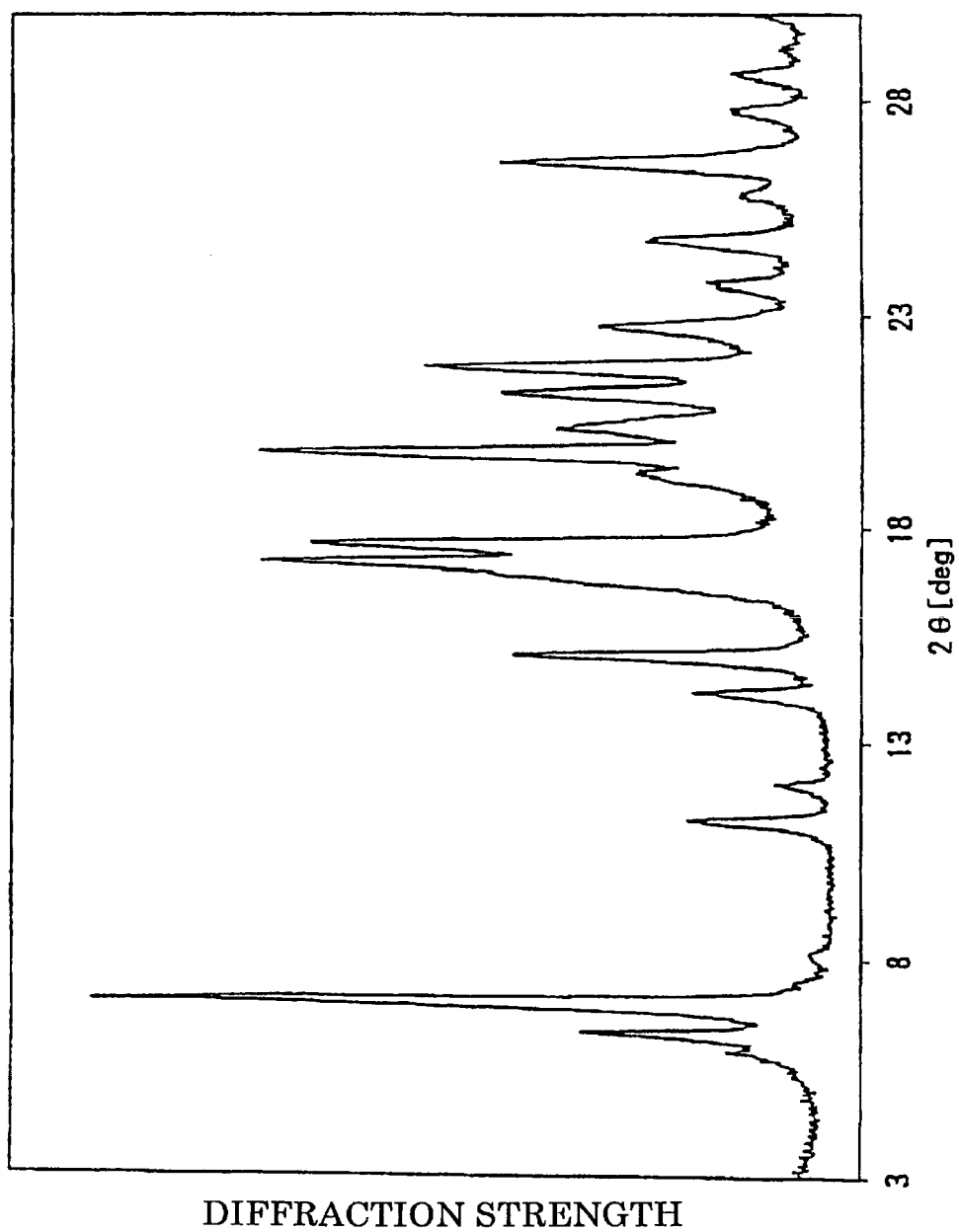
FIG. 2: A powder X-ray diffraction pattern of C-type crystals.

The X-ray diffraction pattern of the dried crystals was measured by powder X-ray diffractometry (diffractometer) using CuK$\alpha$ ray. The thus obtained powder X-ray diffraction pattern is shown in FIG. 2.

As is evident from the pattern of the figure, the dried crystals showed characteristic diffraction peaks at least at 7.1°, 19.8 17.3°, and 17.7°. As described above, the crystals are C-type crystals.

Experimental Example 1

(Dissolution rate of raw (original) powders each from NM C-type crystals and APM, and a mixture thereof) A predetermined amount of the sample was introduced into 900 ml water (20° C.) in a 1-L elution tester (the Japanese Pharmacopoeia, Paddle method, 100 rpm) and its dissolution time was measured (end point was visually confirmed).

Specifically, 1 g of sample taken from each mixture consisting of NM C-type crystal raw powder (average particle size of about 100 $\mu$m) and APM raw powder (average particle size of about 15 $\mu$m, IB-type bundled crystals) at the predetermined various ratios (APM content (% by weight)) shown in Table 1 below, was weighed, and then measured for its dissolution time. For comparison, 1.00 g, 0.90 g, 0.50 g, 0.10 g, 0.03 g, and 0.005 g samples were taken from said NM raw powder, and then their dissolution times were determined in the same manner as above. For the same purpose, 1.00 g, 0.97 g, 0.90 g, 0.50 g, and 0.10 g samples were taken from said APM raw powder, and then their dissolution times were determined in the same manner.

The dissolution time (min) (time needed for the dissolution) of each sample is shown in Table 1 below.

TABLE 1

Dissolution times of NM C-type crystals, APM raw (original) powder, and mixture thereof

| NM C-type crystals alone (original powder) | | APM alone (original powder) | |
| --- | --- | --- | --- |
| Weight of NM C-type crystals | Dissolution time | Weight of APM | Dissolution time |
| 1.00 g | 62 min | 0.10 g | 10 min |
| 0.90 | 60 | 0.50 | 20 |
| 0.50 | 55 | 0.90 | 27 |
| 0.10 | 40 | 0.97 | 29 |
| 0.03 | 30 | 1.00 | 30 |
| 0.005 | 4 | — | — |

| Mixture (1 g) | | | |
| --- | --- | --- | --- |
| Content of APM original powder | Weight of APM | Weight of NM | Dissolution time |
| 10 weight % | 0.10 g | 0.90 g | 25 min |
| 50 | 0.50 | 0.50 | 15 |
| 90 | 0.90 | 0.10 | 8 |
| 97 | 0.97 | 0.03 | 18 |
| 99.5 | 0.995 | 0.005 | 25 |

As can be seen from this table, the dissolution rate (solubility) of the mixture thereof (the sweetener composition of the present invention) is always remarkably and significantly improved as compared with not only those of the NM C-type raw (original) crystals alone but also those of the APM alone.

The degrees of sweetness of NM and APM are respectively about 10,000 and about 200 times that of sucrose, as described above. From this viewpoint, the dissolution time of 1 g mixture should be compared with the dissolution time of an amount of NM necessary to achieve the same degree of sweetness, but even in such comparison, there is the promoting action of APM on the dissolution of NM, as follows. That is, the sweetness of 1 g mixture containing 50% APM raw (original) powder is equal to the sweetness of 0.51 g of NM alone, and the dissolution time of the former is 15 minutes, while the dissolution time of the latter is about 55 minutes, so there is a significant difference therebetween.

Experimental Example 2
(Dissolution rate of raw (original) powders each from NMA-type crystals and APM, and a mixture thereof)

The same experiment as that in Experimental Example 1 was conducted except that NM A-type crystal original powder (average particle size of 100 μm) was used in place of NM C-type crystal original powder.

The dissolution time (min) of each sample is shown in Table 2.

TABLE 2

Dissolution times of NM A-type crystals, APM original powder, and mixture thereof.

| NM A-type crystals alone (original powder) | | APM alone (original powder) | |
|---|---|---|---|
| Weight of NM A-type crystals | Dissolution time | Weight of APM | Dissolution time |
| 1.00 g | 42 min | 0.10 g | 10 min |
| 0.90 | 40 | 0.50 | 20 |
| 0.50 | 35 | 0.90 | 27 |
| 0.10 | 16 | 0.97 | 29 |
| 0.03 | 10 | 1.00 | 30 |
| 0.005 | — | — | — |

| Mixture (1 g) | | | |
|---|---|---|---|
| Content of APM original powder | Weight of APM | Weight of NM | Dissolution time |
| 10 weight % | 0.10 g | 0.90 g | 35 min |
| 50 | 0.50 | 0.50 | 25 |
| 90 | 0.90 | 0.10 | 23 |
| 97 | 0.97 | 0.03 | 29 |
| 99.5 | 0.995 | 0.005 | 30 |

As can be seen from this table, the dissolution rate of the mixture (the sweetener composition of the present invention) is improved remarkably and significantly as compared with NM A-type crystals original powder alone.

It can also be seen that the dissolution rate of the mixture at a range of the certain mixing ratios (50 to 97% by weight of APM) is superior to that of APM powder alone (original powder).

In a similar comparison to that in Experimental Example 1, there is the promoting action of APM on the dissolution of NM, for example, as follows. That is, the sweetness of 1 g mixture containing 50% APM original powder is equal to the sweetness of 0.51 g of NM alone, and the dissolution time of the former is 25 minutes, while the dissolution time of the latter is about 35 minutes, so there is a significant difference therebetween.

Experimental Example 3
(Separate addition of NM original powder and APM original powder)

The same NM and APM as in Experimental Example 1 were used, and the dissolution time was determined in the same manner as that in Experimental Example 1.

That is, 0.5 g each of both of them was weighed (1.0 g in total) and introduced simultaneously without being previously mixed, into the elution tester (separate addition). The results are shown in Table 3 below. For reference, the dissolution time of 0.5 g NM original powder alone (Experimental Example 1) is also shown together in the table.

TABLE 3

Dissolution time of NM and APM when separately added

| NM C-type crystals alone (0.5 g) | Separate addition (1 g in total) (0.5 g NM C-type crystals/0.5 g APM original powder) |
|---|---|
| 55 minutes | 55 minutes |

From this table, the improvement of NM dissolution rate (solubility) by APM is not observed when NM and APM are separately added without being previously mixed.

According to the present invention, Aspartame (APM) is mixed with Neotame (NM) whereby poor dissolution characteristics of NM can be significantly improved, and further, the dissolution rate of APM can also be improved depending on the mixing ratio.

According to the present invention, Aspartame (APM) is mixed with Neotame (NM) whereby the poor dissolution characteristics (solubility) of NM can be significantly improved, and simultaneously a sweetener excellent in quality of sweetness can be easily obtained. Accordingly, the present invention is advantageous particularly for use in drinks where a sweetener is dissolved in industrial production, but the present invention is not limited thereto and can be used as an improved sweetener composition in any uses.

Having now fully described this invention, it will be apparent to one of ordinary skill in the art that many changes and modifications can be made thereto without departing from the spirit or scope of the invention as set forth herein.

This application is based on International Application No. PCT/JP99/02198, filed Apr. 26, 1999, and Japanese Patent Application No. 10-125989, filed May 8, 1998, the entire contents of each of which being hereby incorporated by reference, the same as if set forth at length.

We claim:

1. A sweetener composition, comprising:
   (a) N-[N-(3,3-dimethylbutyl)-L-α-aspartyl]-L-phenyalanine-1-methyl ester; and
   (b) aspartame,
      wherein said aspartame is present in said composition in an amount of 50 to 97% by weight based on the total amount of said aspartame and said N-[N-(3,3-dimethylbutyl)-L-α-aspartyl]-L-phenylalanine 1-methyl ester.

2. The sweetener composition of claim 1, wherein said N-[N-(3,3-dimethylbutyl)-L-α-aspartyl ]-L-phenylalanine 1-methyl ester comprises a C-type crystal.

3. The sweetener composition of claim 1, wherein said N-[N-(3,3-dimethylbutyl)-L-α-aspartyl ]-L-phenylalanine 1-methyl ester is a dry powder.

4. The sweetener composition of claim 1, wherein said aspartame is a dry powder.

5. The sweetener composition of claim 1, wherein said N-[N-(3,3-dimethylbutyl)-L-α-aspartyl ]-L-phenylalanine 1-methyl ester comprises a C-type crystal which exhibits CuKα (2Θ) X-ray diffraction peaks of at least 7.1°, 19.8°, 17.3°, and 17.7°.

6. The sweetener composition of claim 1, wherein said N-[N-(3,3-dimethylbutyl)-L-α-aspartyl ]-L-phenylalanine 1-methyl ester comprises a C-type crystal having a water content of less than 3% by weight.

7. The sweetener composition of claim 1, wherein said N-[N-(3,3-dimethylbutyl)-L-α-aspartyl ]-L-phenylalanine 1-methyl ester comprises an A-type crystal.

8. The sweetener composition of claim 1, wherein said N-[N-(3,3-dimethylbutyl)-L-α-aspartyl ]-L-phenylalanine 1-methyl ester comprises an A-type crystal having a water content in the range of 3 to 6% by weight.

9. The sweetener composition of claim 1, wherein said N-[N-(3,3-dimethylbutyl)-L-α-aspartyl ]-L-phenylalanine 1-methyl ester comprises an A-type crystal which exhibits CuKα (2Θ) X-ray diffraction peaks of at least 6.0°, 24.8°, 8.2°, and 16.5°.

10. The sweetener composition of claim 1, further comprising at least one ingredient selected from the group consisting of diluents, thinners, excipients, sugar alcohols, oligosaccharides, food fibers, dietary fibers, synthetic high-potency sweeteners, Acesulfame K, Alitame, saccharin, low-potency sweeteners, sucrose, glucose and mixtures thereof.

11. A drink composition, comprising:
(A) a mixture, comprising
  (a) N-[N-(3,3-dimethylbutyl)-L-α-aspartyl]-L-phenylalanine 1-methyl ester; and
  (b) aspartame; and
(B) a potable liquid, wherein said aspartame is present in said mixture in an amount of 50 to 97% by weight based on the total amount of said aspartame and said N-[N-(3,3-dimethylbutyl)-L-α-aspartyl]-L-phenylalanine 1-methyl ester.

12. A method for preparing a sweetener composition, comprising:
(1) drying A-type crystals of N-[N-(3,3-dimethylbutyl)-L-α-aspartyl ]-L-phenylalanine 1-methyl ester to obtain C-type crystals of N-[N-(3,3-dimethylbutyl)-L-α-aspartyl]-L-phenylalanine 1-methyl ester; and
(2) mixing said C-type crystals of N-[N-(3,3-dimethylbutyl)-L-α-aspartyl ]-L-phenylalanine 1-methyl ester with aspartame, to obtain said sweetener composition, wherein said aspartame is present in said sweetener composition in an amount of 50 to 97% by weight based on the total weight of said N-[N-(3,3-dimethylbutyl)-L-α-aspartyl ]-L-phenylalanine 1-methyl ester and said aspartame.

13. A method for producing a sweetener, comprising:
mixing N-[N-(3,3-dimethylbutyl)-L-α-aspartyl]-L-phenylalanine 1-methyl ester with aspartame, to obtain said sweetener composition,
wherein said aspartame is present in said sweetener composition in an amount of 50 to 97% by weight based on the total weight of said N-[N-(3,3-dimethylbutyl)-L-α-aspartyl ]-L-phenylalanine 1-methyl ester and said aspartame.

14. The method of claim 13, wherein said N-[N-(3,3-dimethylbutyl)-L-α-aspartyl]-L-phenylalanine 1-methyl ester comprises a C-type crystal having a water content of less than 3% by weight.

15. A method for improving the dissolution rate of N-[N-(3,3-dimethylbutyl)-L-α-aspartyl ]-L-phenylalanine 1-methyl ester, comprising:
mixing said N-[N-(3,3 -dimethylbutyl)-L-α-aspartyl]-L-phenylalanine 1-methyl ester with aspartame, prior to dissolving said N-[N-(3,3-dimethylbutyl)-L-α-aspartyl]-L-phenylalanine 1-methyl ester,
wherein said aspartame is mixed with said N-[N-(3,3-dimethylbutyl)-L-α-aspartyl ]-L-phenylalanine 1-methyl ester in an amount of 50 to 97% by weight based on the total weight of said N-[N-(3,3-dimethylbutyl)-L-α-aspartyl]-L-phenylalanine 1-methyl ester and said aspartame.

16. The method of claim 15, wherein said N-[N-(3,3-dimethylbutyl)-L-α-aspartyl]-L-phenylalanine 1-methyl ester comprises a C-type crystal having a water content of less than 3% by weight.

\* \* \* \* \*

(12) EX PARTE REEXAMINATION CERTIFICATE (6315th)
United States Patent
Ishida et al.

(10) Number: US 6,372,278 C1
(45) Certificate Issued: Jul. 22, 2008

(54) SWEETENER COMPOSITION

(75) Inventors: Hirotoshi Ishida, Kawasaki (JP);
Akihiro Kishishita, Kawasaki (JP);
Takeshi Nagai, Kawasaki (JP);
Kazutaka Nagashima, Kawasaki (JP);
Atsuhiko Hirano, Kawasaki (JP)

(73) Assignee: Ajinomoto Co., Inc., Chuo-Ku, Tokyo (JP)

Reexamination Request:
No. 90/007,164, Aug. 10, 2004

Reexamination Certificate for:
Patent No.: 6,372,278
Issued: Apr. 16, 2002
Appl. No.: 09/707,953
Filed: Nov. 8, 2000

Related U.S. Application Data

(63) Continuation of application No. PCT/JP99/02198, filed on Apr. 26, 1999.

(30) Foreign Application Priority Data

May 8, 1998 (JP) .......................................... 10-125989

(51) Int. Cl.
*A23L 1/236* (2006.01)

(52) U.S. Cl. ............................ 426/548; 426/590; 560/40
(58) Field of Classification Search .................... None
See application file for complete search history.

(56) References Cited

U.S. PATENT DOCUMENTS

| | | | |
|---|---|---|---|
| 2,803,551 A | 8/1957 | Helgren | |
| 3,653,923 A | 4/1972 | Ishii et al. | |
| 3,695,898 A | 10/1972 | Hill et al. | |
| 3,780,189 A | 12/1973 | Scott | |
| 4,001,455 A | 1/1977 | La Via et al. | |
| 4,085,232 A | 4/1978 | Eisenstadt | |
| 4,158,068 A | 6/1979 | Von Rymon Lipinski et al. | |
| 4,254,154 A | 3/1981 | Eisenstadt | |
| 4,495,170 A | 1/1985 | Beyts et al. | |
| 4,835,301 A * | 5/1989 | Wakamatsu et al. ............ | 560/41 |
| 5,474,791 A | 12/1995 | Zablocki et al. | |
| 5,480,668 A | 1/1996 | Nofre et al. .................. | 426/548 |
| 5,510,508 A * | 4/1996 | Claude et al. ................. | 560/41 |
| 5,728,862 A | 3/1998 | Prakash | |
| 6,048,999 A | 4/2000 | Pajor et al. .................... | 560/39 |
| 6,214,402 B1 | 4/2001 | Fotos et al. | |
| 6,372,278 B1 | 4/2002 | Ishida et al. | |
| 6,372,279 B1 | 4/2002 | Ishida et al. | |
| 6,432,464 B1 * | 8/2002 | Andersen et al. ............ | 426/548 |
| 6,444,251 B1 | 9/2002 | Kishishita et al. | |
| 6,692,778 B2 | 2/2004 | Yatka et al. | |
| 2002/0037350 A1 * | 3/2002 | Ishii et al. ................... | 426/548 |

FOREIGN PATENT DOCUMENTS

| | | |
|---|---|---|
| CA | 602572 | 8/1960 |
| EP | 0 139 430 | 9/1984 |
| FR | 2 697 844 | 11/1992 |
| JP | 47-23389 | 6/1972 |
| JP | 8-503206 | 4/1996 |
| JP | 10-248520 | 9/1998 |
| WO | WO 94/11391 | 5/1994 |
| WO | WO 99/30576 | 6/1999 |
| WO | WO 99/30577 | 6/1999 |
| WO | WO 99/62354 | 12/1999 |

OTHER PUBLICATIONS

Schiffman et al. "Investigation of Synergism in Binary Mixtures of Sweeteners" *Brain Research Bulletin* (1995) vol. 38, pp. 105–120.

Wells, A.G.. "The Use of Intense Sweeteners in Soft Drinks," 1989. *Progress in Sweeteners.* Ed. T.H. Grenby. Elsevier Applied Science; London and New York (p. 169–214).

Ager, David J. et al. "Commercial, Synthetic Nonnutritive Sweeteners." *Angewante Chemie International* Ed. 1998, vol. 37; No. 13/14, p. 1802–1817 (Germany).

Ayya, Nalini and Harry T. Lawless. "Quantitative and Quantative Evaluation of High–Intensity Sweeteners and Sweetener Mixtures." *Chemical Senses* 17:245–259, 1992.

Bakal, Abraham I., Ed. Lyn O'Brien Nabors and Robert C. Gelardi. "Mixed Sweetener Functionality." *Alternative Sweeteners.* 2$^{nd}$ ed. Marcel Dekker, NY., (1991) p. 381–399.

Pajor, Laurie, Allison Vevang, and Kernon Gibes. Study Protocols; *Ingestion of Sweetener Candidate NC–00723 in Food and Beverages.* In Memorandum to Ihab Bishay on Dec. 17, 1998.

(Continued)

*Primary Examiner*—Lien Tran

(57) ABSTRACT

One embodiment of the present invention provides a sweetener composition, which includes N-{N-(3,3-dimethylbutyl)-L-α-aspartyl}-L-phenylalanine 1-methyl ester, and Aspartame, wherein a ratio of the Aspartame to a total amount of the Aspartame and the N-{N-(3,3-dimethylbutyl)-L-α-aspartyl}-L-phenylalanine 1-methyl ester is in the range of 10 to 99.5% by weight, methods of making and of using. Another embodiment of the present invention provides a method for preparing a sweetener composition, which includes drying an A-type crystal of N-{N-(3,3-dimethylbutyl)-L-α-aspartyl }-L-phenylalanine 1-methyl ester to obtain a C-type crystal of N-{N-(3,3-dimethylbutyl)-L-α-aspartyl }-L-phenylalanine 1-methyl ester. Another embodiment of the present invention provides a method for producing a sweetener, which includes admixing N-{N-(3,3-dimethylbutyl)-L-α-aspartyl }-L-phenylalanine 1-methyl ester with Aspartame, wherein a ratio of the aspartame to total amount of the N-{N-(3,3-dimethylbutyl)-L-α-aspartyl }-L-phenylalanine 1-methyl ester and the Aspartame is in the range of 10 to 99.5% by weight. Another embodiment of the present invention provides a method for improving the dissolution rate of N-{N-(3,3-dimethylbutyl)-L-α-aspartyl }-L-phenylalanine 1-methyl ester, which includes, prior to dissolving the N-{N-(3,3-dimethylbutyl)-L-α-aspartyl }-L-phenylalanine 1-methyl ester, admixing the N-{N-(3,3-dimethylbutyl)-Lα-aspartyl }-L-phenylalanine 1 methyl ester with Aspartame, wherein a ration of the Aspartame to a total amount of the N-{N-(3,3-dimethylbutyl)-L-α-aspartyl}-L-phenylalanine 1-methyl ester and the Aspartame is in the range of 10 to 99.5% by weight.

OTHER PUBLICATIONS

Third Declaration of D. Eric Walters. Interference No. 105, 246 (RES). Apr. 7, 2005.

Deposition of Masato Kawauchi, Interference No. 105,246 (RES); Apr. 2, 2005.

Lawless, Harry T. and Hildegarde Heymann. "Overview of Sensory Principles and Practices." In *Sensory Evaluation of Food; Principles and Practices*: Aspen Publishers, Inc.: New York 1999, p. 623–646.

Bakal, Abraham I.. "Functionality of Combined Sweeteners in Several Food Applications." *Chemistry and Industry*; Sep. 19, 1983; p. 700–708 (London).

Berenbaum, M.C.. "What is Synergy?" *Pharmacological Reviews*; vol. 1989, No. 41; p. 93–141 (1990) USA.

Chung, Hai–Jung, 51, Food and Science Tech., Abstract of "Measurement of Synergistic Effects of Binary Sweetener Mixtures." *Journal of Food Science and Nutrition*; 1997, 2 (4) 291–295.

Dong, Zedong et al., "Crystal Structure and Physical Characterization of Neotame Methanol Solvate." *Journal of Chemical Crystallography*; vol. 29 No. 8, 1999, p. 967–975.

Dong, Zedong et al. "Crystal Structure of Neotame Anhydrate Polymorph G." *Pharmaceutical Research*, vol. 19, No. 10, Oct. 2002, 1549–1553.

Endicott, C. J. and H. M. Gross. "Artificial Sweetening of Tablets." *Drug and Cosmetic Industry*; (1959) p. 23–25.

Flamm, W. Gary et al. "Long–term Food Consumption and Body Weight Changes in Neotame Safety Studies are Consistent with the Allometric Relationship Observed for other Sweeteners and during Dietary Restrictions." *Regulatory Toxicology and Pharmacology*; 38 (2003) p. 144–156.

Frank, Robert A. et al. "An Assesment of Binary Mixture Interactions for Nine Sweeteners." *Chemical Senses*; vol. 14 No. 5 (1989) p. 621–632.

Fry, John. "Trends and Innovations in Low–Calorie Sweeteners." *The World of Ingredients*; p. 16–18 (Mar.–Apr. 1998).

Gelardi, Robert C. and Editor Neil H. Mermelstein. "The Multiple Sweetener Approach and New Sweeteners on the Horizon." *Food Technology*; Jan. 1987, p. 123–124.

Goodman, Murray et al. "X–Ray Structures of New Dipeptide Taste Ligands." *Journal of Peptide Science*; 4, p. 229–238 (1998).

Grossfeld, J. Abstract of "The Sweetening Power of Artificial Sweeteners." *Z. Ges. Kohlensaure Ind.*; No. 15,253 (1921).

Hornler, Barry E. et al. "Aspartame." *Alternative Sweeteners*, 2nd Edition. Ed. Lyn O'Brien Nabors and Robert C. Gelardi. New York: Marcel Dekker, Inc. 1991. Chapter 4, p. 39–69.

Katritzky, Alan R. et al. "A QSPR Study of Sweetness Potency Using the CODESSA Program." *Croatica Chemica Acta.*, 75 (2), 475–502 (2002).

Mattern, Ralp–Helko, et al. "Conformational Analysis of Potent Sweet Taste Ligands by Nuclear Magnetic Resonance, Computer Simulations and X–Ray Diffraction Studies." *Journal of Peptide Research*: 50 (1997) p. 286–299.

Mayhew, Dale A., et al. "Food Consumption and Body Weight Changes with Neotame, a New Sweetener with Intense Taste: Differentiating Effects of Palatability from Toxicity in Dietary Safety Studies." *Regulatory Toxicology and Pharmacology*: 38 (2003) p. 124–143.

Moncrieff, R. W. *The Chemical Senses*. New York: John Wiley and Sons, Inc. (1941) p. 106–107.

Moskowitz, Howard R., et al. "Sweetness and Acceptance Optimization in Cola Flavored Beverages using Combinations of Artificial Sweeteners—A Psychological Approach." *Journal of Food Quality*; 2 (1978) p. 17–26.

Moskowitz, Howard R. and Leon Klarman. "The Hedonic Tones of Artificial Sweeteners and their Mixtures." *Chemical Senses and Flavor*; 1 (1975) p. 423–429.

"Neotame—First Sightings." *The World of Ingredients* May–Jun. 1999, p. 62.

Nofre, Claude and Jean Marie Tintl. "Neotame: Discovery, Properties, Utility." *Food Chemistry* 69 (2000) p. 245–257.

Padden, Brian E., et al. "Comparison of Solid–State C NMR Spectroscopy and Power X–Ray Diffraction for Analyzing Mixtures of Polymorphs of Neotame." *Analytical Chemistry*: vol. 71 No. 16 (1999) p. 3325–3331.

Paul–Müchen, Theodor. "Physikalische Chemie der Lebensmittel: V. der Süssungsgrad der Süssstoffe." *Zeitschrift Für Elektrochemie*: 27 (1921) p. 539–546.

Prakash, Indra, et al. "Modifying the Temporal Profile of the High–Potency Sweetener Neotame." *Journal of Agricultural and Food Chemistry*; 49 (2001) p. 786–789.

Prakash, Indra, et al. "Neotanm: The Next–Generation Sweetener." *Food Technology*; Jul. 2002, vol. 56, No. 7 p. 36–40 and 45.

Prakash, Indra, et al. "Neotame: Synthesis, Stereochemistry and Sweetness." *Synthetic Communications*; 29 (24) p. 4461–4467 (1999).

Byrne, Maureen. "Sweetener Blends." *Food Engineering International: Food Explorer* Nov. 2, 1998 http://www.food-explorer.com/product/TECHTUT/F102740.htm p. 1–3.

Kim, S.H. and G.E. Dubois. "Natural High Potency Sweeteners." In *Handbook of Sweeteners,* Marie, S. and J.R. Piggot Eds.: Blackie and Son, Ltd.: Glasgow, 1991; p. 116–185.

Schiffman, S. S., et al. "Investigation of Synergism in Binary Mixtures of Sweeteners." *Brain Research Bulletin,* 38(2) (1995) p. 105–120.

Schiffman, S. S. et al. "Sensory Evaluation of Soft Drinks with Varius Sweeteners." *Physiology and Behavior,* 34 (1984) p. 369–377.

Ueno Pharmaceutical Co, Ltd. Technical Dept. "A Novel Method for the Utilization of Artificial Sweeteners." *Shokuhin to Kagaku (Food Science)*, vol. 6, No. 3 (1964) p. 39–43.

Stargel, W. Wayne, et al. "Neotame." In *Alternative Sweeteners*, ed. Nabors L.; Marcel Dekker, Inc.: New York, 2001; p. 129–144.

Tomout, Van, et al. "Sweetness Evaluation of Mixtures of Fructose with Saccharin, Aspartame, or Acesulfame K." *Journal of Food Science*; 50 (1985) p. 469–472.

Verdi, Robert J. and Larry L. Hood. "Advantages of Alternative Sweetener Blends." *Food Technology* Jun. 1993 47(6), p. 94–101.

Vincent, Hugh C., et al. "A Taste Panel Study of Cyclamate–Saccharin Mixture and of its Components," *Journal of the American Pharmaceutical Association* 44(7) Jul. 1955, 442–446.

Walters, Eric, et al. "Active Conformations of Neotame and other High–Potency Sweeteners." *Journal of Medicinal Chemistry*; 43(6) 2000, p. 1242–1245.

Walters, Eric Ed. "High–Intensity Sweetener Blends: Sweet Choices." *Food Product Design* 3(6) 1993, p. 83–92.

Wink, Donald J., et al. "Neotame, an Alkylated Dipeptide and High Intensity Sweetener." *Acta Crystallographica Section C Crystal Structure Communications,* 55(8) 1999, p. 1365–1368.

Yamane, Takeo, et al. Korin–Compendia, entry Kanmiryo (Sweeteners), 1966 p. 216–217, Korinshoin, Tokyo.

Schiffman, Susan S., et al. "Effect of Repeated Presentation on Sweetness Intensity of Binary and Ternary Mixtures of Sweeteners." *Chem. Senses* 28 (2003) 219–229.

DuBois, Grant E., et al. "Concentration–Response Relationships of Sweeteners." In *Sweeteners Discovery, Molecular Design, and Chemoreception* ed. D. Eric Walters, et al. American Chemical Society: Washington, DC (1991) p. 261–276.

Schifferstein, Hendrik N.J. "An Equiratio Mixture Model for Non–additive Components: A Case Study for Aspartame/Acesulfame–K Mixtures." *Chemical Senses* 21(1) 1996 p. 1–11.

Lipinski, G.W. von Rymon. "The Blending of Sweeteners—Applications and Safety Issues." In *Advances in Sweeteners* Ed. T.H. Grenby, et al. Blackie A & P; London (1996) p. 263–272.

Institute of Food Safety and Nutrition. *Combined Actions and Interactions of Chemicals in Mixtures, The Toxicological Effects of Exposure to Mixtures of Industrial and Environmental Chemicals*; Danish Veterinary and Food Administration: Soborg, 2003 p. 1–158.

Hanger, L.Y., et al. "Descriptive Profiles of Selected High Intensity Sweeteners (HIS), HIS Blends, and Sucrose," *Journal of Food Science*, 61(2) 1996, p. 456–464.

Portmann, Marie–Odile and David Kilcast. "Descriptive Profiles of Synergistic Mixtures of Bulk and Intense Sweeteners." *Food Quality and Preference* 19(4) 1998, p. 221–229.

Dubois, Grant E. and Janice F. Lee. "A Simple Technique for the Evaluation of Temporal Taste Properties." *Chemical Senses*, 7(3/4) 1983, p. 237–247.

Noble, A.C., et al. "Factors Affecting the Time–Intensity Parameters of Sweetness: *Sweetener Identity and Concentration, Viscosity, Temperature, Complexity of the System, and Method of Evaluation all Effect the perception of Sweetness."* Food Technology*, Ed. Neil H. Mermelstein, Nov. 1991, p. 121–126.

Chay, Michele and Laurence Hayert. "Magnitude Estimation Appliquée å L'étude de la Saveur Sucrée de la Saccharine, de I'Aspartame et de I'Acésulfame K dans les Boissons Rafraichissantes sans Alcool." *Bios.* 19(3) Mar. 1998, p. 29–33.

Hyvönen, Lea, et al. "Fructose–Saccharin and Xylitol–Saccharin Synergism." *Journal of Food Science,* 43 (1973) p. 251–254.

Askar, A. and M. El–Zoghbl. "Relative Süβe und Synergismus von Fructose oder Xylit mit Aspartam oder Acesulfam–K."

Leatherhead Food International. *High Potency Sweeteners—All you Need to Know*. Lin Tech and/or Connect Consulting; Jun. 4–5, 2003, p. 1.1–10.18.

Duxbury, Dean D. "High–Intensity Sweetener Blends Provide Synergistic Enhancement, *Worldwide Food Applications of Non–Caloric Acesulfame–K Poised for U.S. Market."* Food Processing*, Apr. 1990, p. 36, 38, 40.

Lawless, Harry and Hildegarde Heymann. Appendix 11 "Nonparametric and Binomial–Based Statistical Methods." In *Sensory Evaluation of Food; Principles and Practices,* Aspen Publishers, Inc.: New York, p. 679–700.

Best, Daniel and Lisa Nelson. "Low–Calorie Foods and Sweeteners." *Prepared Foods* 162(7) Jun. 1993: p. 47. LexisNexis.

"Amorphous solid." *McGraw Hill Concise Encyclopedia of Science & Technology.* Ed. Sybil P. Parker. $3^{rd}$ edition, McGraw–Hill, Inc. 1994 p. 84–85.

Birch, Gordon G. "Modulation of Sweet Taste." *BioFactors* 9 (1999) p. 73–80.

Edwards, C.L. and S.J. Palmer. Perceived Taste Intensity and Duration of Nutritive and Non–Nutritive Sweeteners in Water using Time–Intensity (T–I) Evaluations. *Journal of Food Science.* 56(2) 1991, p. 535–542.

Hutteau, F., et al. "Physicochemical and Psychophysical Characteristics of Binary Mixtures of Bulk and Intense Sweeteners." *Food Chemistry,* 63(1) 1998 p. 9–16.

Pariza, Michael W., et al, "Predicting the Functionality of Direct Food Additives." *Food Technology,* 52(11), Nov. 1998, p. 56–60.

Schiffman, Susan S. "Receptors that Mediate Sweetness: Inferences from Biochemical, Electrophysiological and Psychophysical Data." *Pure and Applied Chemistry,* 89(4), 1997, p. 701–708.

Birch, Gordan G. "Role of Water in Sweet Taste Chemoreception." *Pure Appl. Chem.,* 74(7) 2002, p. 1103–1108.

Kilcast, David. "Satisfying Consumer Demands for Sweetness Quality." *AgroFOOD Industry Hi–Tech,* Jul./Aug. 2004, p. 36–38.

Polanski, Jaroslaw, et al. "Self–Organizing Neural Networks for Screening and Development of Novel Artificial Sweetener Candidates." *Combinational Chemistry & High Throughput Screening,* 3(6) 2000, p. 481–495.

Schiffman, Susan, et al. "Selective Inhibition of Sweetness by the Sodium Salt of ±–2(4–Methoxyphenoxy)propanoic Acid." *Chem. Senses,* 24 (1999) p. 439–447.

Carr, B. Thomas, et al. *Sensory Methods for Sweetener Evaluation.* In *Flavor Measurement,* eds. Chi–Tang Ho and Charles H. Manley; Marcel Dekker, Inc.: New York, 1993, p. 219–237.

Haywood, Kieran, ed. *The Optimisation of Sweet Taste Quality Abstracts from the ISOT ECRO 2000 Conference,* Jul. 23, 2000.

O'Carroll, Pat. "Sweetener Trends: Adverse Media Coverage is a Concern." *The World of Food Ingredients,* Feb./Mar. 2000, p. 36–38.

Shiffman, S.S. and C. A. Gatlin, "Sweeteners: State of Knowledge Review." *Neuroscience and Biobehavioral Reviews,* 17 (1993) p. 313–345.

O'Carroll, Pat. "Sweeteners—Synergistic Solutions: Cooperation and Dialouge spur the Development of New Blends and Sweetener Offerings." *The World of Ingredients,* Mar./Apr. 1998, p. 20–23.

Schiffman, Susan S. "Synergism among Ternary Mixtures of Fourteen Sweeteners." *Chem. Senses,* 25 (2000) p. 131–140.

The University of Reading. *The Mechanistic Understanding of the Sweetness Response AIR3–CT94–2107; Final Technical Report.* Jan. 1995–Mar. 1998 p. 1–35.

Lawless, Harry T. "Theoretical Note: Tests of Synergy in Sweetener Mixtures." *Chem. Senses,* 23 (1998) p. 447–451.

Van Dijk, G.J. and M. Rooyakkers. "Sweet Synergy: The Synergy Between Chicory–Based Fructose Syrup and Intensive Sweeteners." *IFI* No. 5 (1996) p. 38–39.

Moskowitz, Howard R. and Leon Klarman. "The Tastes of Artificial Sweeteners and their Mixtures." *Chemical Senses and Flavor* 1(1975) p. 411–412.

Birch, Gordon G. "Towards an Improved Understanding of Sweetener Energy." *Trends in Food Science & Technology* Dec. 1996 vol. 7, p. 403–407.

Machado SG and Robinson GA. An abstract of "A Direct, General Approach Based on Isobolograms for Assessing the Joint Action of Drugs in Pre–Clinical Experiments." *Stat. Med,* Nov. 30, 1994; 13(22); p. 2289–309. PubMED.

Lam GK. An Abstract of the "The Differential Aspects of the Linear Isobole in the Study of Combined Action of Agents." *Bull Math Biol,* Mar. 1993; 55(2) p. 295–313. PubMED.

Suhnel J. An abstract of "Zero Interaction Response Surfaces, Interaction Functions and Difference Response Surfaces for Combinations of Biologically Active Agents." *Arzneimittelforschung* Oct. 1992; 42(10) p. 1251–1258. PubMED.

Poch G., et al. An abstract of "Application of the Isobologram Technique for the Analysis of Combined Effects with Respect to Additivity as well as Independence." *Can. J. Physiol. Pharmacol.* Jun. 1990; 68(6) p. 682–688. PubMED.

Lam GK. An abstract of "Analysis of Interaction of Mixtures of Agents Using the Linear Isobole." *Bull Math Biol.* 1989; 51(3) p. 293–309. PubMED.

Affidavit of Harry T. Lawless in Interference No. 105,246 (RES); Nov. 23, 2004.

Deposition Transcript Eric Walters, Interference No. 105,246; Jan. 25, 2005.

16 CFR 1500.14.

Deposition Transcript Indra Prakash, Interference No. 105,246; Jan. 26, 2005.

Affidavit of Hirotoshi Ishida; Interference No. 105,246 (RES) Feb. 8, 2005.

Second Affidavit of Harry T. Lawless, Interference No. 105,246 (RES); Feb. 10, 2005.

Deposition of Harry T. Lawless, Interference No. 105,246 (RES); Jan. 11, 2005.

Deposition of D. Eric Walters, Interference No. 105,246 (RES); Mar. 16, 2005.

Deposition of Harry T. Lawless, Interference No. 105,246 (RES); Mar. 9, 2005.

Muller, George W., et al. "Carboxylic Acid Replacement Structure—Activity Relationships in Suosan Type Sweeteners. A Sweet Taste Antagonist." *J. Chem. Med.* 35 (1992) p. 1747–1751.

*Ajinomoto Co., Inc.* v. *NutraSweet Company.* Interference No. 105,246 (RES); Decision on Motions Under 37 CFR § 41.125. Filed Jun. 9, 2006.

DeBois. Grant E., et al. "Mechanism of Human Sweet Taste and Implications for Rational Sweetener Design." In *Flavor Measurement,* eds. Chi–Tang Ho and Charles H. Manley; Marcel Dekker, Inc.: New York, 1993, p. 299–266.

Walters, D. Eric. Chapter 6 "Genetically Evolved Receptor Models (GERM) as a 3D QSAR Tool." *Perspective in Drug and Design.* 12/13/14: p. 159–166, 1998.

Walters, Eric D. "Interactions between Sweet and Bitter Tastes." In *Modifying Bitterness; Mechanisms, Ingredients, and Applications.*, ed. Glen Roy, Technomic Publishing Company, Inc. 1997; p. 127–137.

Walters, D. Eric. "Homology–Based Model of the Extracellular Domain of the Taste Receptor T1R3." *Pure Appl. Chem* 74(7) 2002, p. 1117–1123.

Walters, D. Eric. "How are Bitter and Sweet Tastes Related?" *Trends in Food Science & Technology,* (7) Dec. 1996, p. 399–403.

Hallinan, E. Ann. "Investigations of (4–Cyanophenyl) Ureas of Sweet Amino Acids as Potential Sweeteners." *J. Agric. Food Chem.,* 39, 1991 p. 1836–1838.

Chinn, Leland J., et al. "Isovanillyl Sweeteners, Amide Analogues of Dihydrochalcones." *J. Agric. Food Chem.,* 35, 1987 p. 409–411.

Muller, George W., et al. "N,N'–Disubstituted Guanidine High–Potency Sweeteners." *Journal of Medical Chemistry* 35, 1992 p. 740–743.

Roczniak, Steven and D. Eric Walters. "Use of the Specificity Constant Rmax/K, for rigorous comparisons of sweetener potencies." *Chemical Senses* 16(5) 1991, p. 491–495.

O'Brien, Dennis. "Sweet on Sugar Substitute; Alternatives: With Millions Dieting, whoever Finds an Artificial Sweetener with the Taste and Versatility of Sugar is Sure to "Win Big". " *The Baltimore Sun* Jan. 26, 2004; Telegraph, p. 8A. LexisNexis.

Culberson & Walters. "3–D Model for the Sweet Taste Receptor." In *Sweeteners; Discovery, Molecular Design, and Chemoreception,* eds. D. Eric Walters, et al. American Chemical Society 1991, p. 215–223.

Muller, George W., et al. "High–Potency Sweeteners Derived from β–Amino Acids." In *Sweeteners: Discovery, Molecular Design, and Chemoreception,* eds. D. Eric Walters, et al. American Chemical Society 1991, p. 113–125.

Hellekant, Göran, et al. "Electrophysiological Evaluation of Sweeteners." In *Sweeteners: Discovery, Molecular Design, and Chemoreception,* eds.D. Eric Walters, et al. American Chemical Society 1991, p. 290–300.

Walters, D. Eric. "The Rational Discovery of Sweeteners." In *Sweeteners: Discovery, Molecular Design, and Chemoreception,* eds. D. Eric Walters, et al. American Chemical Society 1991, p. 1–11.

Hellekant, Göran and Eric D. Walters. "An Example of Phylogenic Differences in Sweet Taste: Sweetness of Five High–Potency Sweeteres in Rats." In *Sweet–Taste Chemoreception* eds. Mohamed Mathlouth, et al., Elsevier Science Publishers, Ltd.: London 1993, p. 373–386.

DuBois, Grant E., et al. "The Rational Design of Ultra–High–Potency Sweeteners." In *Sweet–Taste Chemoreception* eds. Mohamed Mathlouth, et al., Elsevier Science Publishers, Ltd.: London 1993, p. 237–267.

Walters, Eric D. and Glenn Roy. "Taste Interactions of Sweet and Bitter Compounds." *Flavor–Food Interactions; Developed from a Symposium Sponsored by the Division of Agricultural and Food Chemistry at the 208$^{th}$ National Meeting of the American Chemical Society,* American Chemical Society: Washington, DC, Aug. 21–25, 1994, (1996) p. 130–142.

Ager, David J., et al. "The Synthesis of the High–Potency Sweetener, NC–00637. Part 1: The Synthesis of (S)–2–Methythexanoic Acid." *Organic Process Research and Development,* 7(3) 2003 p. 369–378.

Ager, David J., et al. "The Synthesis of the High–Potency Sweetener, NC–00637. Part 3: The Glutamyl Moiety and Coupling Reactions." *Organic Process Research and Development,* 8(1) 2004 p. 72–85.

Ager, David J., et al. "The Synthesis of the High–Potency Sweetener, NC–00637. Part 2: Preparation of the Pyridine Moiety." *Organic Process Research and Development,* 8(1) 2004 p. 62–71.

Walters, D. Eric. "Using Models to Understand and Design Sweeteners." *Journal of Chemical Education,* 72(8) Aug. 1995 p. 680–682.

Webb, Ginger. "Licorice Extract and Glycyrrhizin Activity." *The Journal of the American Botanical Council*, issue 39, 1997 p. 21.

Beidler, Lloyd M. "Taste Receptor Stimulation." *Progr. Biophysics and Biophysic. Chem*, 12, 1962 p. 109–151.

Declaration of Indra Prakash. Interference No. 105,246 (RES), Nov. 24, 2004.

Declaration of Eric D. Walters. Interference No. 105,246 (RES), Nov. 24, 2004.

Second declaration of Eric D. Walters. Interference No. 105, 246 (RES), Feb. 10, 2005.

Letter to Gibes, Keron and Laurie Pajor from Jeff Hoster. Invention Disclosure of "Sweetness Synergy in Binary Blends of Neotame and other Sweeteners," Oct. 12, 1998.

Horne, John, et al. "Bitter Taste of Saccharin and Acesulfame–K." *Chem. Senses* 27 (2002) p. 31–38.

Deposition of Hirotoshi Ishida. Interference No. 105,246 (RES), Apr. 3, 2005.

*Ajinomoto Co., Inc.* v. *NutraSweet Company*. Interference No. 105,246 (RES); Ajinomoto's Misc. Motion No. 1, Sep. 24, 2004.

*Ajinomoto Co., Inc.* v. *NutraSweet Company*. Interference No. 105,246 (RES); Ajinomoto's Misc. Motion No. 11, Jan. 3, 2005.

*Ajinomoto Co., Inc.* v. *NutraSweet Company*. Interference No. 105,246 (RES); Ajinomoto's Misc. Motion No. 2, Oct. 26, 2004.

*Ajinomoto Co., Inc.* v. *NutraSweet Company*. Interference No. 105,246 (RES); Ajinomoto's Preliminary Motion No. 10, Nov. 24, 2004.

*Ajinomoto Co., Inc.* v. *NutraSweet Company*. Interference No. 105,246 (RES); Ajinomoto's Preliminary Motion No. 3, with appendix A, B, C, and D. Nov. 24, 2004.

*Ajinomoto Co., Inc.* v. *NutraSweet Company*. Interference No. 105,246 (RES); Ajinomoto's Preliminary Motion No. 4, Nov. 24, 2004.

*Ajinomoto Co., Inc.* v. *NutraSweet Company*. Interference No. 105,246 (RES); Ajinomoto's Preliminary Motion No. 5, Nov. 24, 2004.

*Ajinomoto Co., Inc.* v. *NutraSweet Company*. Interference No. 105,246 (RES); Ajinomoto's Preliminary Motion No. 6, Nov. 24, 2004.

*Ajinomoto Co., Inc.* v. *NutraSweet Company*. Interference No. 105,246 (RES); Ajinomoto's Preliminary Motion No. 7, Nov. 24, 2004.

*Ajinomoto Co., Inc.* v. *NutraSweet Company*. Interference No. 105,246 (RES); Ajinomoto's Preliminary Motion No. 8, Nov. 24, 2004.

*Ajinomoto Co., Inc.* v. *NutraSweet Company*. Interference No. 105,246 (RES); Ajinomoto's Preliminary Motion No. 9, with appendix A, B, and C. Nov. 24, 2004.

*Ajinomoto Co., Inc.* v. *NutraSweet Company*. Interference No. 105,246 (RES); Request for Oral Argument for Ajinomoto Motions No. 1–10 and 12, Nov. 17, 2004.

*Ajinomoto Co., Inc.* v. *NutraSweet Company*. Interference No. 105,246 (RES); Ajinomoto's Second Supplemental Notice of Preliminary Motions, Nov. 17, 2004.

*Ajinomoto Co., Inc.* v. *NutraSweet Company*. Interference No. 105,246 (RES); Ajinomoto's Motion No. 12 to Suppress, Apr. 20, 2005.

*Ajinomoto Co., Inc.* v. *NutraSweet Company*. Interference No. 105,246 (RES); Ajinomoto's Reply No. 1 Oct. 18, 2004.

*Ajinomoto Co., Inc.* v. *NutraSweet Company*. Interference No. 105,246 (RES); NutraSweet Preliminary Motion 5, Nov. 24, 2004.

*Ajinomoto Co., Inc.* v. *NutraSweet Company*. Interference No. 105,246 (RES); NutraSweet Preliminary Motion 6, Nov. 24, 2004.

*Ajinomoto Co., Inc.* v. *NutraSweet Company*. Interference No. 105,246 (RES); NutraSweet Preliminary Motion 7, Nov. 24, 2004.

*Ajinomoto Co., Inc.* v. *NutraSweet Company*. Interference No. 105,246 (RES); NutraSweet Provisional Preliminary Motion 8, Nov. 24, 2004.

*Ajinomoto Co., Inc.* v. *NutraSweet Company*. Interference No. 105,246 (RES); NutraSweet's Motion to Exclude or Suppress Evidence No. 10, Apr. 20, 2005.

*Ajinomoto Co., Inc.* v. *NutraSweet Company*. Interference No. 105,246 (RES); NutraSweet's Request for Oral Argument, Apr. 20, 2005.

*Ajinomoto Co., Inc.* v. *NutraSweet Company*. Interference No. 105,246 (RES); NutraSweet Opposition No. 1, Oct. 12, 2004.

*Ajinomoto Co., Inc.* v. *NutraSweet Company*. Interference No. 105,246 (RES); NutraSweet Opposition No. 2, Oct. 27, 2004.

*Ajinomoto Co., Inc.* v. *NutraSweet Company*. Interference No. 105,246 (RES); NutraSweet Opposition No. 3, Feb. 24, 2005.

*Ajinomoto Co., Inc.* v. *NutraSweet Company*. Interference No. 105,246 (RES); NutraSweet Opposition No. 4, Feb. 11, 2005.

*Ajinomoto Co., Inc.* v. *NutraSweet Company*. Interference No. 105,246 (RES); NutraSweet Opposition No. 5, Feb. 11, 2005.

*Ajinomoto Co., Inc.* v. *NutraSweet Company*. Interference No. 105,246 (RES); NutraSweet Opposition No. 6, Feb. 11, 2005.

*Ajinomoto Co., Inc.* v. *NutraSweet Company*. Interference No. 105,246 (RES); NutraSweet Opposition No. 7, Feb. 11, 2005.

*Ajinomoto Co., Inc.* v. *NutraSweet Company*. Interference No. 105,246 (RES); NutraSweet Opposition No. 8, Feb. 11, 2005.

*Ajinomoto Co., Inc.* v. *NutraSweet Company*. Interference No. 105,246 (RES); NutraSweet Opposition No. 9, Feb. 11, 2005.

*Ajinomoto Co., Inc.* v. *NutraSweet Company*. Interference No. 105,246 (RES); NutraSweet Opposition No. 10, Feb. 11, 2005.

*Ajinomoto Co., Inc.* v. *NutraSweet Company*. Interference No. 105,246 (RES); NutraSweet Opposition No. 12, May 11, 2005.

*Ajinomoto Co., Inc.* v. *NutraSweet Company*. Interference No. 105,246 (RES); Ajinomoto's Reply No. 10, Mar. 30, 2005.

*Ajinomoto Co., Inc.* v. *NutraSweet Company*. Interference No. 105,246 (RES); Ajinomoto's Reply No. 2, Nov. 1, 2004.

*Ajinomoto Co., Inc.* v. *NutraSweet Company*. Interference No. 105,246 (RES); Ajinomoto's Preliminary Motion No. 3, Mar. 23, 2005.

*Ajinomoto Co., Inc.* v. *NutraSweet Company*. Interference No. 105,246 (RES); Ajinomoto's Reply No. 4, Mar. 30, 2005.

*Ajinomoto Co., Inc.* v. *NutraSweet Company*. Interference No. 105,246 (RES); Ajinomoto's Reply No. 5, Mar. 30, 2005.

*Ajinomoto Co., Inc.* v. *NutraSweet Company*. Interference No. 105,246 (RES); Ajinomoto's Reply No. 6, Mar. 30, 2005.

*Ajinomoto Co., Inc.* v. *NutraSweet Company*. Interference No. 105,246 (RES); Ajinomoto's Reply No. 7, Mar. 30, 2005.

*Ajinomoto Co., Inc.* v. *NutraSweet Company*. Interference No. 105,246 (RES); Ajinomoto's Reply No. 8, Mar. 30, 2005.

*Ajinomoto Co., Inc.* v. *NutraSweet Company*. Interference No. 105,246 (RES); Ajinomoto's Reply No. 9, Mar. 30, 2005.

*Ajinomoto Co., Inc.* v. *NutraSweet Company*. Interference No. 105,246 (RES); Supplementation of Evidence in Response to NutraSweet's Objection to Exhibits 2002–2004; Oct. 20, 2004.

*Ajinomoto Co., Inc.* v. *NutraSweet Company*. Interference No. 105,246 (RES); Ajinomoto's Reply No. 12, May 25, 2005.

*Ajinomoto Co., Inc.* v. *NutraSweet Company*. Interference No. 105,246 (RES); NutraSweet Misc. Motion 1, Sep. 21, 2004.

*Ajinomoto Co., Inc.* v. *NutraSweet Company*. Interference No. 105,246 (RES); NutraSweet Unopposed Misc. Motion 2, Apr. 13, 2005.

*Ajinomoto Co., Inc.* v. *NutraSweet Company*. Interference No. 105,246 (RES); NutraSweet Misc. Motion 2, Nov. 24, 2004.

*Ajinomoto Co., Inc.* v. *NutraSweet Company*. Interference No. 105,246 (RES); NutraSweet Preliminary Motion 2, Nov. 24, 2004.

*Ajinomoto Co., Inc.* v. *NutraSweet Company*. Interference No. 105,246 (RES); NutraSweet Preliminary Motion 3, Nov. 24, 2004.

*Ajinomoto Co., Inc.* v. *NutraSweet Company*. Interference No. 105,246 (RES); NutraSweet Preliminary Motion 4, Nov. 24, 2004.

*Ajinomoto Co., Inc.* v. *NutraSweet Company*. Interference No. 105,246 (RES); Ajinomoto's Corrected Clean Copy of Claims, Aug. 12, 2004.

*Ajinomoto Co., Inc.* v. *NutraSweet Company*. Interference No. 105,246 (RES); Ajinomoto's Notice Regarding Annotated Claims, Aug. 12, 2004.

*Ajinomoto Co., Inc.* v. *NutraSweet Company*. Interference No. 105,246 (RES); NutraSweet's Designation of Lead and Backup Counsel, Aug. 13, 2004.

*Ajinomoto Co., Inc.* v. *NutraSweet Company*. Interference No. 105,246 (RES); NutraSweet's exhibit list, Apr. 13, 2005.

*Ajinomoto Co., Inc.* v. *NutraSweet Company*. Interference No. 105,246 (RES); NutraSweet's Clean Copy of Claims, Aug. 13, 2005.

*Ajinomoto Co., Inc.* v. *NutraSweet Company*. Interference No. 105,246 (RES); NutraSweet's Notice of Real Party of Interest, Aug. 13, 2004.

*Ajinomoto Co., Inc.* v. *NutraSweet Company*. Interference No. 105,246 (RES); NutraSweet's Request for File Copies, Aug. 13, 2004.

Labuza, Theodore P. and Wendy M. Baisler. "The Kinetics of Nonenzymatic." In *Physical Chemistry of Foods*, New York, NY: Marcel Dekker; p. 595–649, 1992.

*Ajinomoto Co., Inc.* v. *NutraSweet Company*. Interference No. 105,246 (RES); NutraSweet Notice of Filing Priority Statement, Nov. 24, 2004.

*Ajinomoto Co., Inc.* v. *NutraSweet Company*. Interference No. 105,246 (RES); NutraSweet's List of Preliminary Motions, Aug. 13, 2004.

*Ajinomoto Co., Inc.* v. *NutraSweet Company*. Interference No. 105,246 (RES); NutraSweet's Notice of Non–Receipt of File Copy, Aug. 13, 2004.

*Ajinomoto Co., Inc.* v. *NutraSweet Company*. Interference No. 105,246 (RES); NutraSweet's Notice of Serving Additional Literature of Ajinomoto, Nov. 16, 2004.

*Ajinomoto Co., Inc.* v. *NutraSweet Company*. Interference No. 105,246 (RES); NutraSweet Misc. Motion 1 Reply.

*Ajinomoto Co., Inc.* v. *NutraSweet Company*. Interference No. 105,246 (RES); NutraSweet's Reply No. 2, Apr. 13, 2005.

*Ajinomoto Co., Inc.* v. *NutraSweet Company*. Interference No. 105,246 (RES); NutraSweet's Reply No. 3, Apr. 13, 2005.

*Ajinomoto Co., Inc.* v. *NutraSweet Company*. Interference No. 105,246 (RES); NutraSweet's Reply No. 4, Apr. 13, 2005.

*Ajinomoto Co., Inc.* v. *NutraSweet Company*. Interference No. 105,246 (RES); Errata for NutraSweet's Reply No. 4, May 25, 2005.

*Ajinomoto Co., Inc.* v. *NutraSweet Company*. Interference No. 105,246 (RES); NutraSweet's Reply No. 5, Apr. 13, 2005.

*Ajinomoto Co., Inc.* v. *NutraSweet Company*. Interference No. 105,246 (RES); Errata for NutraSweet's Reply No. 5, May 25, 2005.

*Ajinomoto Co., Inc.* v. *NutraSweet Company*. Interference No. 105,246 (RES); NutraSweet's Reply No. 6, Apr. 13, 2005.

*Ajinomoto Co., Inc.* v. *NutraSweet Company*. Interference No. 105,246 (RES); NutraSweet's Reply No. 7, Apr. 13, 2005.

*Ajinomoto Co., Inc.* v. *NutraSweet Company*. Interference No. 105,246 (RES); NutraSweet's Reply No. 8 to Ajinomoto's Opposition No. 8 to NutraSweet's Provisional Preliminary Motion No. 8, Mar. 30, 2005.

*Ajinomoto Co., Inc.* v. *NutraSweet Company*. Interference No. 105,246 (RES); NutraSweet's Reply No. 10, May 25, 2005.

*Ajinomoto Co., Inc.* v. *NutraSweet Company*. Interference No. 105,246 (RES); NutraSweet's Responses to Ajinomoto's Obervations, May 11, 2005.

*Ajinomoto Co., Inc.* v. *NutraSweet Company*. Interference No. 105,246 (RES); Ajinomoto's Objections to NutraSweet's Exhibits, Dec. 2, 2004.

*Ajinomoto Co., Inc.* v. *NutraSweet Company*. Interference No. 105,246 (RES); Ajinomoto's Objections to NutraSweet's Exhibits to NutraSweet Opposition Nos. 4–9, Feb. 18, 2005.

*Ajinomoto Co., Inc.* v. *NutraSweet Company*. Interference No. 105,246 (RES); Ajinomoto's Objections to NutraSweet's Exhibits to NutraSweet Replies Nos. 2–7, Apr. 20, 2005.

*Ajinomoto Co., Inc.* v. *NutraSweet Company*. Interference No. 105,246 (RES); Ajinomoto's Opposition No. 1, Oct. 12, 2004.

*Ajinomoto Co., Inc.* v. *NutraSweet Company*. Interference No. 105,246 (RES); Ajinomoto's Opposition No. 2 to NutraSweet's Preliminary Motion No. 2 Alleging Obviousness of Ajinomoto's Claims, Feb. 11, 2005.

*Ajinomoto Co., Inc.* v. *NutraSweet Company*. Interference No. 105,246 (RES); Ajinomoto's Opposition No. 3 to NutraSweet Preliminary Motion No. 3, Feb. 11, 2005.

*Ajinomoto Co., Inc.* v. *NutraSweet Company*. Interference No. 105,246 (RES); Ajinomoto's Opposition No. 4 to NutraSweet Preliminary Motion No. 3, Feb. 11, 2005.

*Ajinomoto Co., Inc.* v. *NutraSweet Company*. Interference No. 105,246 (RES); Ajinomoto's Opposition No. 5 to NutraSweet Preliminary Motion No. 5, Feb. 11, 2005.

*Ajinomoto Co., Inc.* v. *NutraSweet Company*. Interference No. 105,246 (RES); Ajinomoto's Opposition No. 6 to NutraSweet's Preliminary Motion No. 6 for Judgment that Ajinomoto Claims 15–39 are Unpatentable under 35 USC §112, ¶ 2, Feb. 11, 2005.

*Ajinomoto Co., Inc.* v. *NutraSweet Company*. Interference No. 105,246 (RES); Ajinomoto's Opposition No. 7 to NutraSweet's Preliminary Motion No. 7 for Judgment that Ajinomoto Claims 15–39 are Unpatentable under 35 USC §112, ¶ 1, Feb. 11, 2005.

*Ajinomoto Co., Inc.* v. *NutraSweet Company*. Interference No. 105,246 (RES); Ajinomoto's Opposition No. 8 to NutraSweet's Preliminary Motion No. 8 for Judgment that Ajinomoto Claim 40 is invalid under 35 USC §135(b), Feb. 11, 2005.

*Ajinomoto Co., Inc.* v. *NutraSweet Company*. Interference No. 105,246 (RES); Ajinomoto's Opposition No. 10 to NutraSweet's Motion to Exclude or Suppress, May 11, 2005.

*Erstellung eines Compartmentmodells des Süßintensität beliebiger Mischungen ausgewähiter süßer in wässriger Lösung.* Sep. 9, 2001.

*Ajinomoto Co., Inc.* v. *NutraSweet Company*. Interference No. 105,246 (RES); Judgment Under 37 CFR §41.127. Filed Jun. 9, 2006.

\* cited by examiner

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–16 are cancelled.

* * * * *